United States Patent
Xu et al.

(10) Patent No.: US 9,855,539 B2
(45) Date of Patent: *Jan. 2, 2018

(54) SEPARATION DEVICE FOR USE IN FLUIDIZED BED REACTOR, REACTION REGENERATION APPARATUS AND PROCESS FOR PREPARING OLEFINS, AND PROCESS FOR PREPARING AROMATIC HYDROCARBONS

(71) Applicants: CHINA PETROLEUM & CHEMICAL CORPORATION, Beijing (CN); Shanghai Research Institute of Petrochemical Technology, SINOPEC, Shanghai (CN)

(72) Inventors: Jun Xu, Shanghai (CN); Songyuan Gu, Shanghai (CN); Siqing Zhong, Shanghai (CN); Yongming Jin, Shanghai (CN); Zhinan Yu, Shanghai (CN); Guozhen Qi, Shanghai (CN); Xiaohong Li, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/881,605

(22) Filed: Oct. 13, 2015

(65) Prior Publication Data

US 2016/0101396 A1   Apr. 14, 2016

(30) Foreign Application Priority Data

Oct. 14, 2014   (CN) .......................... 2014 1 0539938

(51) Int. Cl.
*B01J 8/24* (2006.01)
*B01J 8/26* (2006.01)
(Continued)

(52) U.S. Cl.
CPC ............ *B01J 8/0015* (2013.01); *B01J 8/0055* (2013.01); *B01J 8/26* (2013.01); *C07C 1/20* (2013.01);
(Continued)

(58) Field of Classification Search
USPC .......................................... 208/161
See application file for complete search history.

(56) References Cited

U.S. PATENT DOCUMENTS 3,607,129 A * 9/1971 Carson ................... B01J 8/0055
208/155
3,888,762 A * 6/1975 Gerhold ..................... B01J 8/26
208/120.01

(Continued)

FOREIGN PATENT DOCUMENTS

CN        101164685 A    4/2008
CN        103121901 A    5/2013

*Primary Examiner* — Jennifer A Leung
(74) *Attorney, Agent, or Firm* — Buchanan Ingersoll & Rooney PC (57) ABSTRACT

Device for use in a fluidized bed reactor includes a gas-solid separator communicated with an outlet of the fluidized bed reactor; a vertically arranged damper, a solid outlet of the gas-solid separator communicated with a lower region of the damper, a gas outlet of the gas-solid separator communicated with an upper region of the damper; a fine gas-solid separator, an inlet of the fine gas-solid separator communicated with the upper region of the damper, and a solid outlet of the fine gas-solid separator communicated with the lower region of the damper. Product from the fluidized bed reactor is fed into the preliminary gas-solid separator, most solid catalysts separated and fed into the lower region; the product (Continued)

entraining the rest catalysts is fed into the upper region, and into the fine gas-solid separator, the rest catalysts fed into the lower region; and final product is obtained from the fine gas-solid separator.

40 Claims, 5 Drawing Sheets

(51) Int. Cl.
*B01J 8/00* (2006.01)
*C07C 1/20* (2006.01)
*C10G 11/18* (2006.01)

(52) U.S. Cl.
CPC ... *C10G 11/182* (2013.01); *B01J 2208/00752* (2013.01); *B01J 2208/00938* (2013.01); *B01J 2208/00991* (2013.01); *C07C 2529/40* (2013.01); *C07C 2529/85* (2013.01); *Y02P 20/52* (2015.11); *Y02P 30/42* (2015.11)

(56) References Cited

U.S. PATENT DOCUMENTS

| | | | | | |
|---|---|---|---|---|---|
| 4,118,338 | A | * | 10/1978 | Gross | B01J 8/26 208/120.01 |
| 4,502,947 | A | * | 3/1985 | Haddad | C10G 11/18 208/161 |
| 4,764,268 | A | * | 8/1988 | Lane | C10G 11/18 208/113 |
| 6,146,519 | A | * | 11/2000 | Koves | B01J 8/0055 208/113 |
| 6,166,282 | A | | 12/2000 | Miller | |

\* cited by examiner

SEPARATION DEVICE FOR USE IN FLUIDIZED BED REACTOR, REACTION REGENERATION APPARATUS AND PROCESS FOR PREPARING OLEFINS, AND PROCESS FOR PREPARING AROMATIC HYDROCARBONS

CROSS REFERENCE TO RELATED APPLICATION

The present application claims benefit of Chinese patent application CN 201410539938.0, entitled Multiregion Coupling Reinforcing Process for Preparing Olefins from Methanol, and filed on Oct. 14, 2014, the entirety of which is incorporated herein by reference.

TECHNICAL FIELD

The present disclosure relates to the technical field of chemical engineering, and in particular, to a separation device for use in a fluidized bed reactor. The present disclosure further relates to a reaction regeneration apparatus comprising said separation device, and a process for preparing olefins as well as a process for preparing aromatic hydrocarbons.

BACKGROUND OF THE INVENTION

In modern petrochemical engineering, ethylene and propylene are the most crucial basic materials. Ethylene can be used in preparing downstream products including polyethylene, styrene, vinyl acetate, ethylene oxide, and ethylene glycol, and the like. Propylene can be used in preparing downstream products including polypropylene, acrylonitrile, propylene oxide, and isopropyl alcohol, and the like. Ethylene and propylene and downstream products thereof are widely used in the fields of industry and agriculture, transportation, and national defense.

In recent years, the demand for ethylene and propylene remains high. Under the circumstance that oil resource gradually decreases, the short supply of oil in China can be greatly relieved through coal chemical technology, with which ethylene and propylene can be prepared from non-oil resource. This is significant in promoting the development of the national heavy chemical industry. Based on the coal chemical technology, methanol can be prepared from coal, and then olefins can be prepared from methanol.

At present, an apparatus for preparing olefins from methanol is similar to a catalytic cracking device, both being continuous reaction-regeneration type. According to patent literature U.S. Pat. No. 6,166,282, a process and a reactor for converting oxides to low carbon olefins are disclosed. A fast fluidized bed reactor is used in the above patent literature. Gas reacts in a reaction zone with low gas velocity, and then rises to a fast separation zone with rapidly decreasing inner diameter. Catalysts entrained in product are separated through a preliminary cyclone. Because the product and the catalysts are separated rapidly, secondary reaction can be effectively prevented. The reactor used in the above patent literature is an upflow fast fluidized bed reactor with a traditional feed inlet.

Chinese patent literature CN103121901A recites a method for converting oxygenated chemicals to generate low-carbon olefins. According to the above method, to-be-generated catalysts and regenerated catalysts are premixed in a catalyst blender, and then enter a reactor, thereby the problems of undermixing of catalysts and low yield of low-carbon olefins in a reaction zone in the prior art can be solved.

Chinese patent literature CN101164685A relates to a combined quick fluidized bed reactor for methyl alcohol or dimethyl ether catalytic reaction. According to the above patent literature, a separation device in a settling zone is arranged externally, so that space occupied by the settler can be reduced, thereby a settling velocity of catalysts can be increased, and residence time of olefins can be reduced. In the meantime, problems of low selectivity and low yield of ethylene and propylene can also be solved. As compared with a traditional quick fluidized bed reactor with external settler, the yield of ethylene can be increased by 4% and that of propylene can be increased by 3%.

In the prior art, in order to improve the settling separation effect of catalysts, the settler is structured with large size and large inner space. However, in this case, gas flow velocity in the settler is relatively small, causing long residence time of gas inside the settler. Consequently, secondary reaction of product with entrained catalysts would easily occur. The product finally obtained would therefore contain a lot of impurities, which is quite adverse to the preparation of olefins and aromatic hydrocarbons.

SUMMARY OF THE INVENTION

Directed against the above problem, a separation device for use in a fluidized bed reactor is provided according to the present disclosure. When product leaves the fluidized bed reactor, catalysts entrained in the product is rapidly separated through the separation device. In this case, the product will not experience a secondary reaction, so that the final product can contain fewer impurities. In addition, the present disclosure further relates to a reaction regeneration apparatus comprising the separation device, as well as a process for preparing olefins and a process for preparing aromatic hydrocarbons.

In a first aspect according to the present disclosure, a separation device for use in a fluidized bed reactor is provided. The separation device comprises a preliminary gas-solid separator communicated with an outlet of the fluidized bed reactor, a vertically arranged damper, a solid outlet of the preliminary gas-solid separator being communicated with a lower region of the damper, and a gas outlet of the preliminary gas-solid separator being communicated with an upper region of the damper, and a fine gas-solid separator, an inlet of the fine gas-solid separator being communicated with the upper region of the damper and a solid outlet of the fine gas-solid separator being communicated with the lower region of the damper. The separation device is configured so that product having catalysts entrained therein from the fluidized bed reactor is fed into the preliminary gas-solid separator, most solid catalysts being separated and fed into the lower region of the damper; the product entraining the rest catalysts is fed into the upper region of the damper, and into the fine gas-solid separator, the rest catalysts being separated and fed into the lower region of the damper; and final product is obtained from the outlet of the fine gas-solid separator.

According to the present disclosure, catalysts entrained in the product from the fluidized bed reactor can be rapidly removed therefrom through the preliminary gas-solid separator and the fine gas-solid separator of the separation device. As compared with a settling separation in the prior art, the separation device according to the present disclosure has the advantages of higher separation speed, whereby secondary reaction of the product under the catalysis of catalysts to be regenerated that are still active can be effectively prevented. In this case, with higher separation speed, the production efficiency can be greatly improved. In addition, the product from the fluidized bed reactor usually has high velocity, thereby impacting the device accepting the high velocity product to an extent of intense vibration. As a result, the device may even be damaged. According to the present disclosure, a damper is disposed between the preliminary gas-solid separator and the fine gas-solid separator, so that the impact of the high velocity product can be absorbed by the preliminary gas-solid separator and the damper together, whereby damage to the entire separation device can be prevented. It is unnecessary that the preliminary gas-solid separator and the damper be made large sized.

In an embodiment according to the present disclosure, a diameter of the upper region of the damper is smaller than that of the lower region thereof. Preferably, a ratio of the diameter of the upper region to that of the lower region is in a range of 0.05 to 0.5. Fluctuation caused by the product flowing quickly from the fluidized bed reactor into the upper region of the damper can be rapidly decreased due to the smaller diameter of the upper region, so that the lower region of the damper can remain in a relatively placid state. As a result, the catalysts can be stably accommodated in the lower region of the damper, and the gas-solid separation efficiency can be improved.

In an embodiment according to the present disclosure, the lower region of the damper is configured so that it can perform a steam stripping operation. For example, a steam inlet can be disposed on a lower end of the damper, and structure or component for use in a steam stripping operation can be disposed inside the lower region of the damper. The structure or component is well known to the person skilled in the art. Steam, such as water vapor, is feed into the lower region of the damper through the lower end thereof, so that product entrained in the catalysts can be separated. The separated product rises with the water vapor to the upper region of the damper and mixes with the product therein. In this case, a yield of the product can be greatly increased. In addition, as described above, the damper is configured so that severe fluctuation in the lower region thereof can be prevented, thereby facilitating the stream stripping operation.

In an embodiment according to the present disclosure, a position where the gas outlet of the preliminary gas-solid separator is connected with the damper is below a position where the inlet of the fine gas-solid separator is connected with the damper. Based on the above configuration, catalysts entrained in the product can be precipitated as the product flowing upward in the damper, which further increases the gas-solid separation efficiency.

In an embodiment according to the present disclosure, both the preliminary gas-solid separator and the fine gas-solid separator are single cyclone separators. In a preferred embodiment, the fine gas-solid separator comprises two- or multi-stage series cyclone separators. The two- or multi-stage series cyclone separators are configured so that an inlet of a first stage cyclone separator is communicated with the upper region of the damper, the final product being obtained from a gas outlet of a last stage cyclone separator, a gas outlet of an upstream cyclone separator is communicated with a gas inlet of an adjacent downstream cyclone separator, and solid outlets of all the cyclone separators are communicated with the lower region of the damper. A cyclone separator can facilitate rapid separation of catalysts from the product, and has the advantages of simple structure and low price. Furthermore, the effect of separating catalysts from the product can be improved through multiple series cyclone separators. As a result, catalyst recovery efficiency can be improved, and the final product obtained can contain fewer impurities.

In an embodiment according to the present disclosure, the upper region of the damper is provided with an inlet port for communicating with the gas outlet of the preliminary gas-solid separator, and the inlet port is configured to be tangent to a side wall of the upper region. The product from the fluidized bed reactor can be fed into the upper region of the damper through said inlet port in a path that is tangent to the side wall of the upper region thereof. As a result, the impact of the product on the damper can be reduced, so that the vibration of the damper can be alleviated. In addition, rotating product can also facilitate the precipitation of the catalysts therein, thereby further improving the gas-solid separation efficiency.

In a second aspect according to the present disclosure, a reaction regeneration apparatus is further proposed. The reaction regeneration apparatus comprises the abovementioned separation device, and further comprises a fluidized bed reactor and a catalyst regeneration device. The fluidized bed reactor comprises an inlet zone at a lower position, an outlet zone at an upper position, and a reaction zone between the inlet zone and the outlet zone, the outlet zone being communicated with the preliminary gas-solid separator of the separation device. The catalyst regeneration device comprises a feed zone at a lower position and a discharge zone at an upper position, the feed zone being arranged lower than the lower region of the damper, and the discharge zone being arranged higher than the inlet zone of the fluidized bed reactor. The lower region of the damper is communicated with the feed zone of the catalyst regeneration device through a second pipe, and the discharge zone of the catalyst regeneration device is communicated with the inlet zone of the fluidized bed reactor through a third pipe.

In an embodiment according to the present disclosure, the third pipe is provided with a flow blocking member at a top of an inner wall thereof. The flow blocking member is used for blocking gas and catalysts from flowing backwards into the third pipe caused by strong reaction in the fluidized bed reactor. In this case, a feed rate of catalyst particles can be effectively increased, so that a circulating rate of the catalysts can be further increased, whereby the yield of the product can be increased.

In an embodiment according to the present disclosure, the flow blocking member is a baffle tilting towards the fluidized bed reactor. In a specific example, a ratio of an area of the baffle to an area of a cross section of the third pipe is in a range of 0.1 to 1. The baffle is sector shaped or rectangular. A ratio of a distance between the baffle and the fluidized bed reactor to a length of the third pipe is in a range of 0.01 to 0.5. An angle formed between the baffle and an axis of the third pipe is in a range of 10 to 75 degrees. Preferably, provided is a plurality of baffles arranged in parallel with respect to one another.

In another embodiment according to the present disclosure, the flow blocking member is a stop pawl protruding radially inward. Preferably, provided is a plurality of stop pawls arranged in a row along the axis of the third pipe. In an embodiment, a ratio of a length of each stop pawl to a diameter of the third pipe is in a range of 0.1 to 0.5. Preferably, a cross section of each of the stop pawls is in a shape of a triangle, a rectangle, or a sector.

In another embodiment according to the present disclosure, the outlet zone of the fluidized bed reactor is provided with an inlet for accelerating gas. Preferably, the inlet for accelerating gas is configured to extend obliquely from a lower position towards an upper position. High speed gas, such as nitrogen, inert gases, or water vapor, can be injected into the outlet zone of the fluidized bed reactor through the inlet for accelerating gas, so that a pressure in the fluidized bed reactor can be more uniform, and the catalysts can be more evenly distributed in the fluidized bed reactor. In this case, the defect of a fluidized bed reactor in the prior art, i.e., a density of catalysts at a top of the fluidized bed reactor is relatively small, while a density of catalysts at a bottom thereof is relatively large, can be eliminated. On the whole, by arranging the inlet for accelerating gas, the catalysts can spread evenly along an axial direction of the fluidized bed reactor, so that gas-solid contact efficiency can be optimized. In the meantime, a rate of circulation of catalysts in the entire reaction regeneration apparatus can be improved, and the yield of the product can be increased.

In an embodiment, the inlet for accelerating gas forms an angle in a range of 5 to 39 degrees relative to a longitudinal axis of the fluidized bed reactor. In another embodiment, a ratio of a diameter of the inlet for accelerating gas to a diameter of the outlet zone of the fluidized bed reactor is in a range of 0.01 to 0.1. In a further embodiment according to the present disclosure, a length of a part of the outlet zone of the fluidized bed reactor that is above the inlet for accelerating gas divided by an overall length of the outlet zone of the fluidized bed reactor is in a range of 0.1 to 0.8.

In an embodiment according to the present disclosure, a guide plate with through holes is disposed between the inlet zone and the reaction zone of the fluidized bed reactor. Catalysts can be evenly distributed in a radial direction of the fluidized bed reactor through the guide plate, so that the yield of product can be further increased.

In an embodiment according to the present disclosure, the inlet zone of the fluidized bed reactor is disposed lower than the lower region of the damper, and the lower region of the damper is communicated with the inlet zone of the fluidized bed reactor through a first pipe. This apparatus can be used for preparing olefins from methanol.

In an embodiment according to the present disclosure, the first pipe, the second pipe, and the third pipe each are provided with a valve for controlling material flow.

In a third aspect according to the present disclosure, a process for preparing olefins is proposed, using said reaction regeneration apparatus. An inlet zone of a fluidized bed reactor is disposed lower than a lower region of a damper, and the lower region of the damper is communicated with the inlet zone of the fluidized bed reactor through a first pipe. The process comprises the steps of reacting raw material containing oxygenates with catalysts in a reaction zone of the fluidized bed reactor; feeding product obtained and entrained catalysts into a separation device through an outlet zone of the fluidized bed reactor; separating the product from the entrained catalysts through the separation device, wherein a part of catalysts obtained from the separation is directly fed into the inlet zone of the fluidized bed reactor, and the rest catalysts are regenerated, and then fed into the inlet zone of the fluidized bed reactor; and mixing non-regenerated catalysts and regenerated catalysts in the inlet zone of the fluidized bed reactor, and then feeding the mixed catalysts into the reaction zone of the fluidized bed reactor.

In an embodiment according to the present disclosure, a weight ratio of the non-regenerated catalysts to the regenerated catalysts is in a range of 0.3 to 1.5.

In an embodiment according to the present disclosure, an operation of the separation device comprises the following steps. Product from the fluidized bed reactor having catalysts entrained therein is preliminarily separated through a preliminary gas-solid separator. Then, product entraining the rest catalysts after the preliminary separation is fed into the upper region of the damper. Next, the product is drawn out from the damper, and fed into a fine gas-solid separator for fine separation. Subsequently, the product is obtained from a gas outlet of the fine gas-solid separator, and catalysts from the preliminary gas-solid separator and the fine gas-solid separator are gathered into the lower region of the damper.

In an embodiment according to the present disclosure, water vapor is fed into the damper from a lower end thereof, so that product entrained in the catalysts is separated from the catalysts.

In an embodiment according to the present disclosure, a pressure in the fluidized bed reactor indicated by gage pressure is in a range of 0-0.4 MPa, an average temperature therein is in a range of 380-550° C., and a mean density in the reaction zone is in a range of 40-200 $KG/m^3$. The catalyst used therein is SAPO-34, a catalyst regeneration medium being air and a regeneration temperature being in a range of 600-700° C.

In an embodiment according to the present disclosure, an inlet for accelerating gas is disposed in the outlet zone of the fluidized bed reactor, and gas flowing into the outlet zone of the fluidized bed reactor through the inlet for accelerating gas is water vapor or nitrogen, a linear speed of the gas being in a range of 1.0-10.0 m/s.

In an embodiment according to the present disclosure, the oxygenates comprises one or more selected from a group consisting of methanol, ethanol, n-propyl alcohol, isopropyl alcohol, C4-C20 alcohol, ethyl methyl ether, dimethyl ether, diethyl ether, diisopropyl ether, methanal, dimethyl carbonate, acetone, and acetic acid, and a weight of the oxygenates accounts for 10 to 100% of the raw material.

In a fourth aspect according to the present disclosure, a process for preparing aromatic hydrocarbons is proposed, using said reaction regeneration apparatus. the process comprises: reacting raw material containing oxygenates with catalysts in a reaction zone of a fluidized bed reactor; feeding product obtained and entrained catalysts into a separation device through an outlet zone of the fluidized bed reactor; and separating the product from the catalysts entrained therein through the separation device, wherein the catalysts obtained from the separation is regenerated and fed into the inlet zone of the fluidized bed reactor, and subsequently into the reaction zone of the fluidized bed reactor.

In an embodiment according to the present disclosure, an operation of the separation device comprises the following steps. Product from the fluidized bed reactor having catalysts entrained therein is preliminarily separated through a preliminary gas-solid separator. Then, product entraining the rest catalysts after the preliminary separation is fed into the upper region of the damper. Next, the product is drawn out from the damper, and fed into a fine gas-solid separator for fine separation. Subsequently, the final product is obtained from a gas outlet of the fine gas-solid separator, and catalysts from the preliminary gas-solid separator and the fine gas-solid separator are gathered into the lower region of the damper.

In an embodiment according to the present disclosure, water vapor is fed into the damper from a lower end thereof, so that product entrained in the catalysts is separated from the catalysts.

In an embodiment according to the present disclosure, a pressure in the fluidized bed reactor indicated by gage pressure is in a range of 0-0.6 MPa, an average temperature therein is in a range of 440-550° C., a space velocity in the reaction zone is in a range of 0.3-5 h$^{-1}$, a mean density in the reaction zone is in a range of 200-450 kg/m$^3$. The catalyst used therein is ZSM-5, a catalyst regeneration medium being air and a regeneration temperature being in a range of 550-650° C.

In an embodiment according to the present disclosure, an inlet for accelerating gas is disposed in the outlet zone of the fluidized bed reactor, and gas flowing into the outlet zone of the fluidized bed reactor through the inlet for accelerating gas is vapor or nitrogen, a linear speed of the gas being in a range of 1.0-10.0 m/s.

In an embodiment according to the present disclosure, the oxygenates comprises one or more selected from a group consisting of methanol, ethanol, n-propyl alcohol, isopropyl alcohol, C4-C20 alcohol, ethyl methyl ether, dimethyl ether, diethyl ether, diisopropyl ether, methanal, dimethyl carbonate, acetone, and acetic acid, and a weight of the oxygenates accounts for 10 to 100% of the raw material.

As compared with the prior art, the present disclosure has the following advantages. When product leaves the fluidized bed reactor, catalysts entrained in the product is rapidly separated through the separation device. In this case, the product will not experience a secondary reaction, so that the final product can contain fewer impurities.

BRIEF DESCRIPTION OF THE DRAWINGS

The present disclosure will be further described in detail based on the examples in view of the accompanying drawings. In the drawings.

In the drawings, the same components are indicated with the same reference sign. The drawings are not drawn to actual scale.

DETAILED DESCRIPTION OF THE EMBODIMENTS

The present disclosure will be further described in view of the accompanying drawings.

Figure 1:
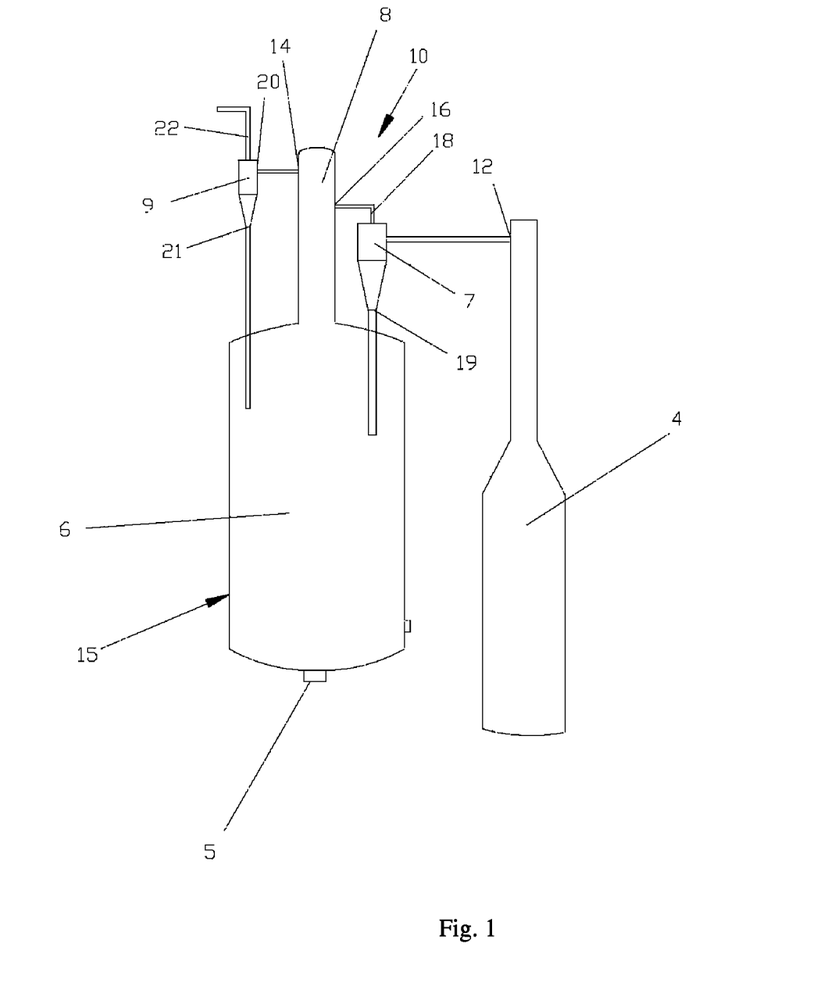
FIG. 1 schematically shows a separation device for use in a fluidized bed reactor according to example 1 of the present disclosure, FIG. 2 schematically shows the separation device for use in a fluidized bed reactor according to example 2 of the present disclosure, FIG. 3 schematically shows a reaction regeneration apparatus according to example 1 of the present disclosure.

As shown in FIG. 1, a separation device 10 according to example 1 of the present disclosure is usually used together with a fluidized bed reactor 4. Specifically, the separation device 10 is configured to receive product having catalysts entrained therein from a product outlet 12 of the fluidized bed reactor 4. After the product flows through the separation device 10, the catalysts entrained therein are separated therefrom. The separation device 10 will be described in detail below.

As shown in FIG. 1, the separation device 10 comprises a preliminary gas-solid separator 7, a damper 15, and a fine gas-solid separator 9 disposed in an order according to a flow direction of the product. The preliminary gas-solid separator 7 is directly communicated with the fluidized bed reactor 4 for receiving the product from the fluidized bed reactor 4. The damper 15 is vertically arranged, and an inlet port 16 is arranged in an upper region 8 of the damper 15. A gas outlet 18 of the preliminary gas-solid separator 7 is communicated with the inlet port 16, and a solid outlet 19 of the preliminary gas-solid separator 7 is communicated with a lower region 6 of the damper 15. An outlet port 14 is further disposed in the upper region 8 of the damper 15 in a position deviated from the inlet port 16. An inlet 20 of the fine gas-solid separator 9 is communicated with the outlet port 14 in the upper region 8 of the damper 15, and a solid outlet 21 of the fine gas-solid separator 9 is communicated with the lower region 6 of the damper 15.

In the example as shown in FIG. 1, the preliminary gas-solid separator 7 is a cyclone separator, and the fine gas-solid separator 9 can also be a cyclone separator. The cyclone separator 7 and the cyclone separator 9 can have a same specification or different specifications. In an example, if the cyclone separator 9 has different specification from the cyclone separator 7, the cyclone separator 9 may be selected to be able to separate particles of smaller particle size as compared with the cyclone separator 7.

During the operation of the separation device 10, product from the fluidized bed reactor 4 having catalysts entrained therein is fed into the preliminary gas-solid separator 7 first. Most catalyst particles are separated from the product in the preliminary gas-solid separator 7, and then fed into the lower region 6 of the damper 15. The product carries the rest small amount of catalysts into the upper region 8 of the damper 15. The product slows down a bit in the upper region 8, and subsequently enters into the fine gas-solid separator 9. The rest catalysts are separated from the product, and fed into the lower region 6 of the damper 15. Final product is obtained from a gas outlet 22 of the fine gas-solid separator 9.

Because the preliminary gas-solid separator 7 and the fine gas-solid separator 9 can both be cyclone separators, the separation rate of catalysts from the product can be greatly increased. As a result, the product will not experience a secondary reaction, and the final product can contain very few impurities.

Preferably, a position where the gas outlet 18 of the preliminary gas-solid separator 7 is connected with the damper 15 is below a position where the inlet 20 of the fine gas-solid separator 9 is connected with the damper 15. As a whole, the preliminary gas-solid separator 7 is disposed at a lower position, and the fine gas-solid separator 9 is disposed at a higher position. In this case, product from the preliminary gas-solid separator 7 can only move upwards in the upper region 8 of the damper 15, so as to go out of the damper 15 and into the fine gas-solid separator 9. During the movement of the product, the rest catalysts entrained therein can be precipitated. As a result, the gas-solid separation efficiency can be improved.

Preferably, the inlet port 16 in the upper region 8 of the damper 15 is configured to be tangent to a side wall of the upper region 8. In this case, product from the fluidized bed reactor 4 can be fed into the upper region 8 in a path that is tangent to the side wall of the upper region 8. As a result, the impact of the product on the damper 15 and the upper region 8 can be reduced, so that the vibration of the damper 15 can be alleviated.

The damper 15 can be a variable diameter container. As shown in FIG. 1, a diameter of the upper region 8 of the damper 15 is smaller than that of the lower region 6 thereof. A ratio of the diameter of the upper region 8 to that of the lower region 6 is in a range of 0.05 to 0.5. For example, the ratio can be 0.08, 0.1, 0.12, or 0.3. As a whole, the upper region 8 looks like a tubular piece vertically arranged on the lower region 6. The reason for configuring the above structure for the damper 15 is that the upper region 8 can actually function as a gas flow passage rather than a container for accommodating substances, while the lower region 6 can function as a container for accommodating catalysts. A damper 15 with such structure can have a far smaller sized settler than a damper in the prior art, whereby the production cost of the apparatus can be reduced.

In a preferred example, a steam inlet 5 is disposed at a lower end of the damper 15, and structure or component (not shown in the drawings) for use in a steam stripping operation can be disposed in the lower region 6 or an interior of the damper 15. The structure or component is well known to the person skilled in the art, thus will not be described in detail herein. In this case, the lower region 6 of the damper 15 can form a stripper, so that a steam stripping can be performed on the product entrained in the catalysts in the lower region 6 in the process of the gas-solid separation, thereby further improving the yield of product. In a specific example, water vapor can be used in the steam stripping.

Figure 2:
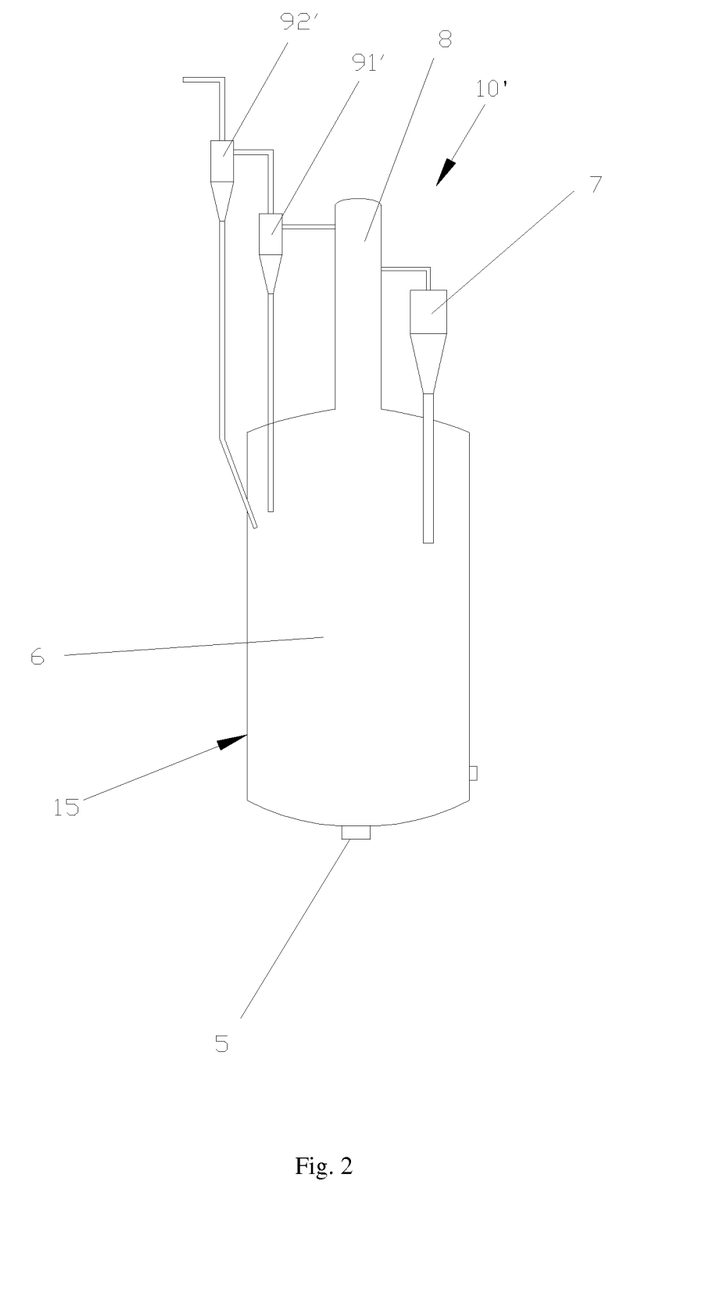

FIG. 2 shows a separation device 10'. FIG. 2 does not show a fluidized bed reactor coordinating with the separation device 10'. However, it is easy to understand that a connection mode between the separation device 10' and the fluidized bed reactor is the same as that between the separation device 10 and the fluidized bed reactor as shown in FIG. 1, which will not be described in detail herein.

The separation device 10' is different from the separation device 10 only in a fine gas-solid separator thereof. In the separation device 10' as shown in FIG. 2, a fine gas-solid separator thereof comprises two- or multi-stage series cyclone separators (FIG. 2 merely schematically shows two-stage cyclone separators 91' and 92'). These separators can all be cyclone separators, or a combination of multiple types of separators.

As shown in FIG. 2, the two- or multi-stage series cyclone separators are configured so that an inlet of a first stage cyclone separator 91' is communicated with the upper region 8 of the damper 15, product being obtained from a gas outlet of a second cyclone separator 92'. In addition, a gas outlet of the first stage cyclone separator 91' is communicated with an inlet of the second stage cyclone separator 92'. Solid outlets of both the first stage cyclone separator 91' and the second stage cyclone separator 92' are communicated with the lower region 6 of the damper 15. It should be noted that the first stage cyclone separator 91' is selected to separate catalysts with relatively large mass, and the second stage cyclone separator 92' is selected to separate catalysts with relatively small mass. Multi-stage series cyclone separators have similar structure as the two-stage series cyclone separators, thus will not be described in detail herein.

Such fine gas-solid separator can improve the separation effect of catalysts from the product, thereby further increasing catalyst recovery efficiency. In the meantime, the final product obtained contains fewer impurities.

Figure 3:
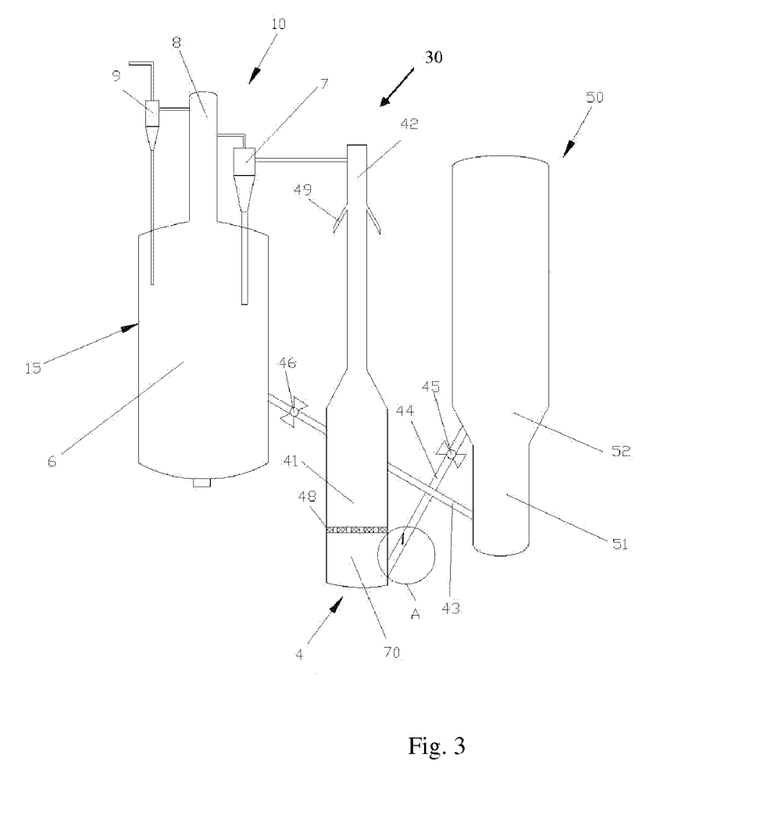

FIG. 3 schematically shows a reaction regeneration apparatus 30 according to example 1 of the present disclosure. As shown in FIG. 3, the reaction regeneration apparatus 30 comprises the separation device 10, the fluidized bed reactor 4, and a catalyst regeneration device 50, as well as pipes for connecting the separation device 10, the fluidized bed reactor 4, and the catalyst regeneration device 50.

The fluidized bed reactor 4 comprises an inlet zone 70 at a lower position, an outlet zone 42 at an upper position, and a reaction zone 41 between the inlet zone 70 and the outlet zone 42. The outlet zone 42 is communicated with the preliminary gas-solid separator 7 of the separation device 10. Raw material and catalysts react in the reaction zone 41 and generate product. The product entrains a portion of the catalysts and leaves the fluidized bed reactor 4 from the outlet zone 42.

The catalyst regeneration device 50 comprises a feed zone 51 at a lower position and a discharge zone 52 at an upper position. The catalyst regeneration device 50 is used to reactivate the catalysts which have lost activity due to previous use in the fluidized bed reactor 4.

In order to save energy, the feed zone 51 is arranged lower than the lower region 6 of the damper 15 and the discharge zone 52 is arranged higher than the inlet zone 70 of the fluidized bed reactor 4, so that gravity can be taken full advantage of to drive catalysts to flow among the separation device 10, the fluidized bed reactor 4, and the catalyst regeneration device 50. In addition, the lower region 6 of the damper 15 is communicated with the feed zone 51 of the catalyst regeneration device 50 through a second pipe 43, and the discharge zone 52 of the catalyst regeneration device 50 is communicated with the inlet zone 70 of the fluidized bed reactor 4 through a third pipe 44. In this case, deactivated catalysts can enter into the catalyst regeneration device 50 from the damper 15 through the second pipe 43 under gravity and be regenerated therein. The regenerated catalysts automatically enter into the fluidized bed reactor 4 from the catalyst regeneration device 50 through the third pipe 44. In the entire process, the catalysts need to be elevated only in the catalyst regeneration device 50. Since the catalysts are light weighted, it merely takes high pressure gas from a bottom of the catalyst regeneration device 50 to elevate the catalysts. Hence, power consumption for driving the flow of catalysts can be greatly reduced, and the device can be simplified. Although the second pipe 43 and the third pipe 44 seem to be crossed as shown in FIG. 3, in the actual apparatus, the second pipe 43 and the third pipe 44 are not crossed, but rather two straight lines in different planes.

The reaction regeneration apparatus 30 as shown in FIG. 3 can be used for preparing aromatic hydrocarbons from oxygenates. Because preparation of aromatic hydrocarbons requires catalysts with high activity, the catalysts fed into the fluidized bed reactor 4 must be completely regenerated. A process for preparing aromatic hydrocarbons from oxygenates using the reaction regeneration apparatus 30 will be described in detail below.

It should be understood that the second pipe 43 is provided with a control valve 46, and the third pipe 44 is provided with a control valve 45, so that the flow of the catalysts can be controlled.

Figure 4:
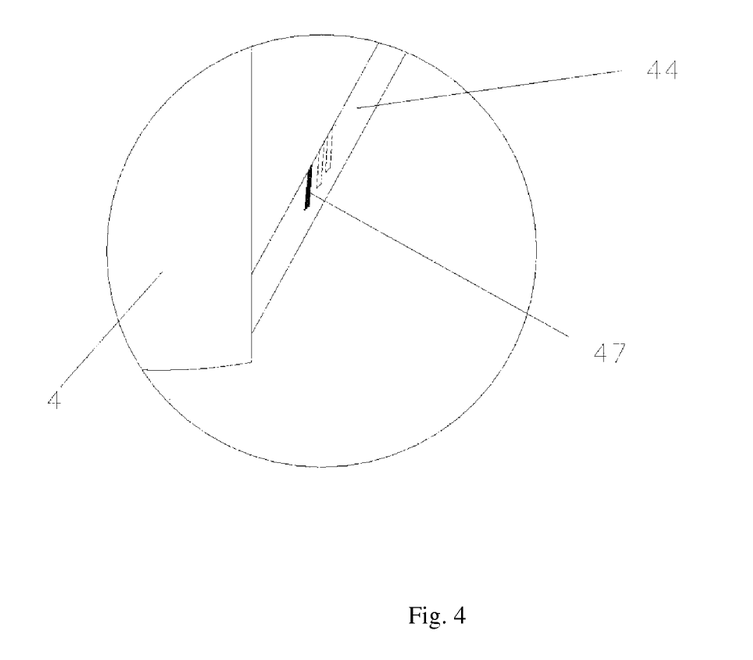
FIG. 4 shows an enlarged view of part A in FIG. 3 according to an example of the present disclosure.
Figure 5:
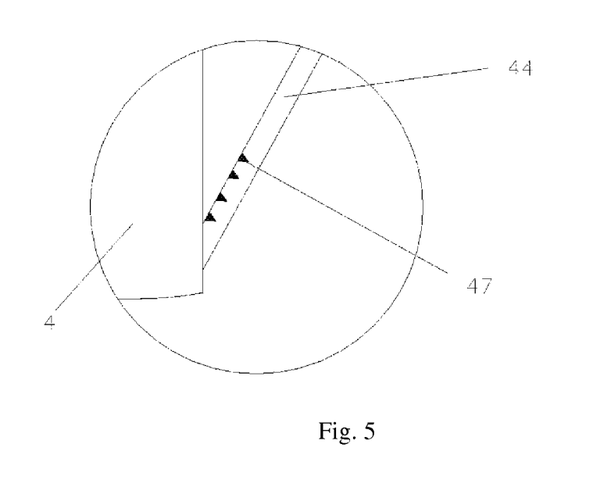
FIG. 5 shows an enlarged view of part A in FIG. 3 according to another example of the present disclosure, and FIG. 6 schematically shows the reaction regeneration apparatus according to example 2 of the present disclosure.

As shown in FIG. 4 and FIG. 5, the third pipe 44 is provided with a flow blocking member 47 tilting towards the fluidized bed reactor 4 at a top of an inner wall thereof. FIG. 4 shows an example of the flow blocking member 47. According to the example as shown in FIG. 4, the flow blocking member 47 is in a form of a baffle 47. The baffle 47 can effectively block the gas and catalysts flowing backwards into the third pipe 44 caused by strong reaction in the fluidized bed reactor 4, so that a circulating rate of catalysts can be increased, thereby further increasing the yield of product. In a specific example, a ratio of an area of the baffle 47 to an area of a cross section of the third pipe 44 is in a range of 0.1 to 1, for example, the ratio can be 0.3, 0.45, or 0.8. In addition, the baffle 47 is sector shaped or rectangular, or even semicircular. A ratio of a distance between the baffle 47 and the fluidized bed reactor 4 to a length of the third pipe 44 is in a range of 0.01 to 0.5, for example, the ratio can be 0.2, 0.3, or 0.4. An angle formed between the baffle 47 and an axis of the third pipe 44 is in a range of 10 to 75 degrees, for example, the angle can be 15 degrees, 10 degrees, 30 degrees, or 45 degrees. It should be understood that there can also be a plurality of baffles 47 arranged in parallel as shown by the dashed line in FIG. 4.

FIG. 5 shows another example of the flow blocking member 47. As shown in FIG. 5, the flow blocking member 47 can be configured as a stop pawl radially protruding from a top of an inner wall of the third pipe 44. There can be a plurality of stop pawls 47 arranged in a row along an axis of the third pipe 44. In order to effectively block the gas and catalysts flowing backwards from the fluidized bed reactor 4 to the third pipe 44, a ratio of a length of each stop pawl 47 to a diameter of the third pipe 44 is configured in a range of 0.1 to 0.5, and a cross section of each of the stop pawls 47 is in a shape of a triangle, a rectangle, or a sector.

A guide plate 48 with through holes is disposed between the inlet zone 70 and the reaction zone 41 of the fluidized bed reactor 4. The guide plate 48 can facilitate an even distribution of the catalysts along an axial direction of the fluidized bed reactor 4, so that the yield of product can be further improved.

The outlet zone 42 of the fluidized bed reactor 4 is provided with an inlet 49 for accelerating gas. Preferably, the inlet 49 for accelerating gas is configured to extend obliquely from a lower position towards an upper position. In this case, gas of relatively high velocity can be injected into the outlet zone 42 of the fluidized bed reactor 4 through the inlet 49 for accelerating gas, so that a pressure in the fluidized bed reactor 4 can be more uniform, and the catalysts can be more evenly distributed in the fluidized bed reactor 4. As a result, the yield of product can also be higher. The inlet 49 for accelerating gas forms an angle in a range of 5 to 39 degrees relative to a vertical direction (i.e., a longitudinal axis of the fluidized bed reactor 4), for example, the angle can be 10 or 15 degrees. A diameter of the inlet 49 for accelerating gas is smaller than that of the outlet zone 42. For example, a ratio of the diameter of the inlet 49 for accelerating gas to that of the outlet zone 42 can be 0.05 or 0.1. A ratio of a length L1 of a part of the outlet zone 42 of the fluidized bed reactor 4 that is above the inlet 49 for accelerating gas to an overall length L2 of the outlet zone 42 of the fluidized bed reactor 4 is in a range of 0.1 to 0.8. For example, the ratio can be 0.1 or 0.4.

Figure 6:
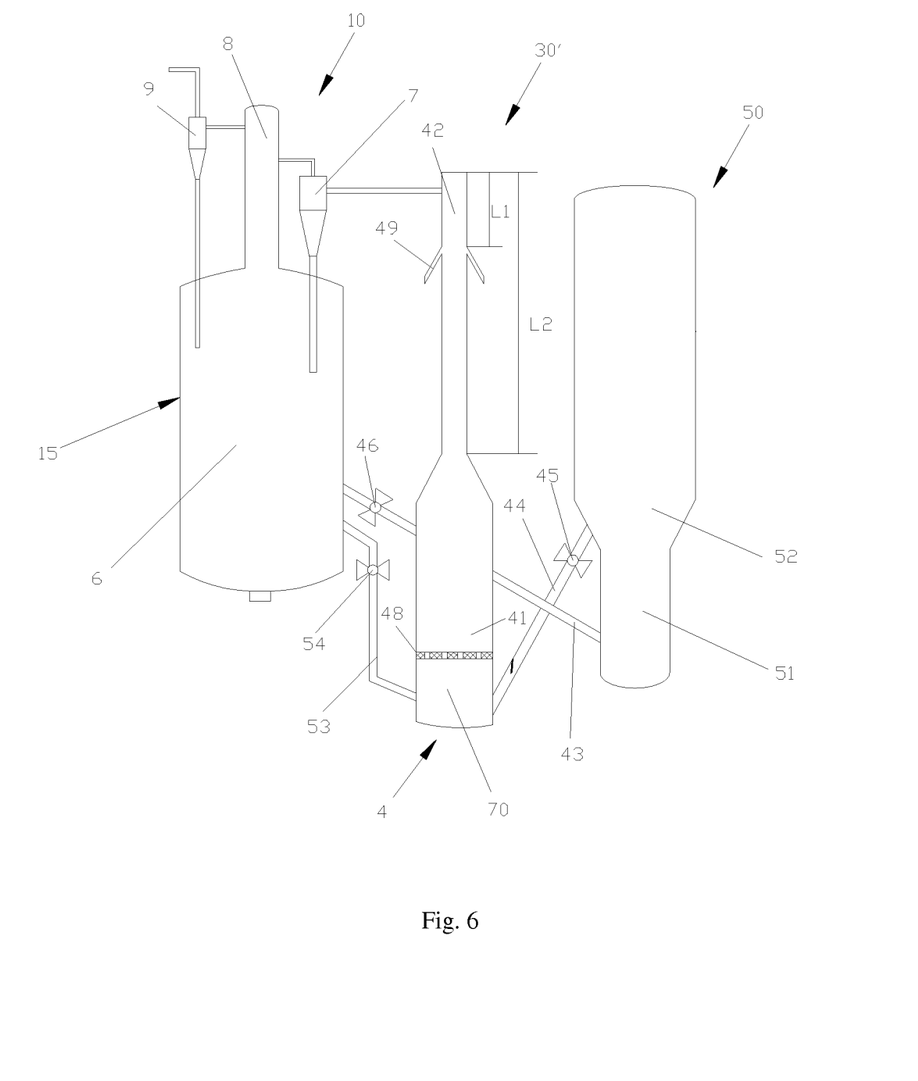

FIG. 6 schematically shows a reaction regeneration apparatus 30' according to example 2 of the present disclosure. The reaction regeneration apparatus 30' is similar to the reaction regeneration apparatus 30 as shown in FIG. 3 in structure. The difference only lines in that the inlet zone 70 of the fluidized bed reactor 4 is disposed lower than the lower region 6 of the damper of the separation device 10, and the lower region 6 of the damper is communicated with the inlet zone 70 of the fluidized bed reactor 4 through a first pipe 53. A control valve 54 is disposed on the first pipe 53.

The reaction regeneration apparatus 30' as shown in FIG. 6 can be used for preparing olefins from oxygenates. Because preparation of olefins requires catalysts with moderate activity, the catalysts fed into the fluidized bed reactor 4 should comprise non-regenerated catalysts, so that the overall activity of the catalysts can be reduced. A process for preparing olefins from methanol using the reaction regeneration apparatus 30' will be described in detail.

The process for preparing aromatic hydrocarbons from methanol will be described based on the reaction regeneration apparatus as shown in FIG. 3.

Methanol and catalysts react in the reaction zone 41 of the fluidized bed reactor 4. In an example, the catalysts are ZSM-5. A pressure in the fluidized bed reactor 4 indicated by gage pressure is in a range of 0-0.6 MPa, an average temperature therein is in a range of 440-550° C., a space velocity in the reaction zone is in a range of 0.3-5 h$^{-1}$, and a mean density in the reaction zone is in a range of 200-450 kg/m$^3$ Product obtained and catalysts entrained in the product are fed into the separation device 10 through the outlet zone 42 of the fluidized bed reactor 4. An operation of the separation device 10 comprises the following steps. First, product from the fluidized bed reactor 4 having catalysts entrained therein is preliminarily separated through the preliminary gas-solid separator 7. Next, the product entraining the rest catalysts after the preliminary separation is fed into the upper region 8 of the damper 15. Subsequently, the product is drawn from the damper 15, and fed into the fine gas-solid separator 9 for fine separation. The product is obtained from the gas outlet of the fine gas-solid separator 9, and catalysts from the preliminary gas-solid separator 7 and the fine gas-solid separator 9 are gathered into the lower region 6 of the damper 15.

Catalysts in the lower region 6 of the damper 15 are fed into the catalyst regeneration device 50 through the second pipe 43 to be regenerated. In an example, a catalyst regeneration medium is air, and a regeneration temperature is in a range of 550-650° C.

Regenerated catalysts are fed into the inlet zone 70 of the fluidized bed reactor 4 through the third pipe 44. Subsequently, the regenerated catalysts can be pushed by feed gas, such as methanol, into the reaction zone 41 of the fluidized bed reactor 4 again for reaction.

In a preferred example, an inlet 49 for accelerating gas is disposed in the outlet zone 42 of the fluidized bed reactor 4. Gas flowing into the outlet zone 42 of the fluidized bed reactor 4 through the inlet 49 for accelerating gas is water vapor or nitrogen, a linear speed of the gas being in a range of 1.0-10.0 m/s.

In another preferred example, water vapor is fed into the damper 15 from a lower end thereof, so that product entrained in the catalysts is separated from the catalysts.

The process for preparing olefins from methanol will be described based on the reaction regeneration apparatus as shown in FIG. 6. In the reaction regeneration apparatus as shown in FIG. 6, the inlet zone 70 of the fluidized bed reactor 4 is disposed lower than the lower region 6 of the damper 15, and the lower region 6 of the damper 15 is communicated with the inlet zone 70 of the fluidized bed reactor 4 through the first pipe 53.

Methanol and catalysts react in the reaction zone 41 of the fluidized bed reactor 4. In an example, the catalysts are molecular sieve, such as SAPO-34. A pressure in the fluidized bed reactor 4 indicated by gage pressure is in a range of 0-0.4 MPa, an average temperature therein is in a range of 380-550° C., and a mean density in the reaction zone is in a range of 40-200 kg/m$^3$.

Product obtained and catalysts entrained in the product are fed into the separation device 10 through the outlet zone 42 of the fluidized bed reactor 4. An operation of the separation device 10 comprises the following steps. First, product from the fluidized bed reactor 4 having catalysts entrained therein is preliminarily separated through the preliminary gas-solid separator 7. Next, the product entraining the rest catalysts after the preliminary separation is fed into the upper region 8 of the damper 15. Subsequently, the product is drawn from the damper 15, and fed into the fine gas-solid separator 9 for fine separation. The final product is obtained from the gas outlet of the fine gas-solid separator 9, and catalysts from the preliminary gas-solid separator 7 and the fine gas-solid separator 9 are gathered into the lower region 6 of the damper 15.

A part of the catalysts in the lower region 6 of the damper 15 is fed directly into the inlet zone 70 of the fluidized bed reactor 4 through the first pipe 53. The rest catalysts are fed into the catalyst regeneration device 50 through the second pipe 43 to be regenerated. Regenerated catalysts are fed into the inlet zone 70 of the fluidized bed reactor 4 through the third pipe 44 and mixed with non-regenerated catalysts. In an example, a catalyst regeneration medium is air and a regeneration temperature is in a range of 600-700° C.

Subsequently, the catalysts in the inlet zone 70 can be pushed by feed gas, such as methanol, into the reaction zone 41 of the fluidized bed reactor 4 again for reaction.

In a preferred example, an inlet 49 for accelerating gas is disposed in the outlet zone 42 of the fluidized bed reactor 4. Gas flowing into the outlet zone 42 of the fluidized bed reactor 4 through the inlet 49 for accelerating gas is water vapor or nitrogen, a linear speed of the gas being in a range of 1.0-10.0 m/s.

In another preferred example, water vapor is fed into the damper 15 from a lower end thereof, so that product entrained in the catalysts can be separated from the catalysts.

The inventor implemented the example for preparing olefins using the process according to the present disclosure and the reaction regeneration apparatus as shown in FIG. 6, and made comparison with the process for preparing olefins in the prior art. In the examples, raw materials and catalysts for each experiment are the same, and experiment parameters are conventional parameters for the reaction.

Data relevant to the reaction regeneration apparatus and the yield of the product are indicated in Table I.

sure is not limited to the specific examples disclosed herein, but rather includes all the technical solutions falling within the scope of the claims.

The invention claimed is:

1. A separation device for use in a fluidized bed reactor, comprising
    a preliminary gas-solid separator communicated with an outlet of the fluidized bed reactor,
    a vertically arranged damper, a solid outlet of the preliminary gas-solid separator being communicated with a lower region of the damper, and a gas outlet of the preliminary gas-solid separator being communicated with an upper region of the damper, and
    a fine gas-solid separator, an inlet of the fine gas-solid separator being communicated with the upper region of the damper, and a solid outlet of the fine gas-solid separator being communicated, with the lower region of the damper, wherein
    the separation device is configured so that product having catalysts entrained therein from the fluidized bed reactor is fed into the preliminary gas-solid separator, most solid catalysts being separated and fed into the lower region of the damper; the product entraining the rest catalysts is fed into the upper region of the damper, and into the fine gas-solid separator, the rest catalysts being separated and fed into the lower region of the damper; and final product is obtained from a gas outlet of the fine gas-solid separator;
    wherein the upper region of the damper is provided with an inlet port for communicating with the gas outlet of the preliminary gas-solid separator, and the inlet port is configured to be tangent to a side wall of the upper region.

TABLE I

|  | Guide plate 48 | Inlet 49 for accelerating gas | Baffle 47 | Ratio of diameter of the upper region of the damper to that of the lower region thereof | Preliminary gas-solid separator 7 | Fine gas-solid separator 9 | Yield |
|---|---|---|---|---|---|---|---|
| Examples |  |  |  |  |  |  |  |
| 1 | Yes | 4 | Yes | 0.12 | Yes | Yes | 84.11% |
| 2 | Yes | 8 | Yes | 0.3 | Yes | Yes | 83.16% |
| 3 | Yes | 4 | Yes | 0.1 | Yes | Yes | 82.95% |
| 4 | Yes | 4 | Yes | 0.08 | Yes | Yes | 84.94% |
| 5 | Yes | 4 | Yes | 0.1 | Yes | Yes | 85.07% |
| Comparison examples |  |  |  |  |  |  |  |
| 1 | No | 0 | No | Settler | No | No | 80.63% |
| 2 | No | 0 | No | Settler | No | No | 80.08% |

As shown in Table I, using the reaction regeneration apparatus and the process of the present disclosure, the yield of olefins can be remarkably increased. For example, the yield of olefins can be increased by 5% at most, which is a huge improvement to chemical enterprises with large output.

Although the present disclosure has been described in view of preferred embodiments, various modifications and variants to the present disclosure may be made by anyone skilled in the art, without departing from the scope and spirit of the present disclosure. In particular, as long as there is no structural conflict, various embodiments as well as the respective technical features mentioned herein may be combined with one another in any manner. The present disclo- 2. The separation device according to claim 1, wherein a diameter of the upper region of the damper is smaller than that of the lower region thereof.

3. The separation device according to claim 2, wherein a ratio of the diameter of the upper region to that of the lower region is in a range of 0.05 to 0.5.

4. The separation device according to claim 1 wherein a position where the gas outlet of the preliminary gas-solid separator is connected with the damper is below a position where the inlet of the fine gas-solid separator is connected with the damper.

5. The separation device according to claim 1, wherein both the preliminary gas-solid separator and the fine gas-solid separator are single cyclone separators.

6. The separation device according to claim 1, wherein the preliminary gas-solid separator is a cyclone separator, and the fine gas-solid separator comprises two-or multi-stage series cyclone separators, wherein
the two-or multi-stage series cyclone separators are configured so that an inlet of a first stage cyclone separator is communicated with the upper region of the damper, the final product being obtained from a gas outlet of a last stage cyclone separator, a gas outlet of an upstream cyclone separator is communicated with a gas inlet of an adjacent downstream cyclone separator, and solid outlets of all the cyclone separators are communicated with the lower region of the damper.

7. The separation device according to claim 1, wherein the lower region of the damper is configured and arranged to perform a steam stripping operation.

8. A reaction regeneration apparatus, comprising the separation device according to claim 1, and further comprising a fluidized bed reactor and a catalyst regeneration device, wherein
the fluidized bed reactor comprises an inlet zone at a lower position, an outlet zone at an upper position, and a reaction zone between the inlet zone and the outlet zone, the outlet zone being communicated with the preliminary gas-solid separator of the separation device, and
the catalyst regeneration device comprises a feed, zone at a lower position and a discharge zone at an upper position, the feed zone being arranged lower than the lower region of the damper, and the discharge zone being arranged higher than the inlet zone of the fluidized bed reactor,
wherein, the lower region of the damper is communicated with the feed zone of the catalyst regeneration device through a second pipe, and the discharge zone of the catalyst regeneration device is communicated with the inlet zone of the fluidized bed reactor through a third pipe.

9. The reaction regeneration apparatus according to claim 8, wherein the outlet zone of the fluidized bed reactor is provided with an inlet for accelerating gas.

10. The reaction regeneration apparatus according to claim 9, wherein the inlet for accelerating gas is configured to extend obliquely from a lower position towards an upper position.

11. The reaction regeneration apparatus according to claim 10, wherein the inlet for accelerating gas forms an angle in a range of 5 to 39 degree relative to a longitudinal, axis of the fluidized bed reactor.

12. The reaction regeneration apparatus according to claim 9, wherein a ratio of a diameter of the inlet for accelerating gas to a diameter of the outlet zone of the fluidized bed reactor is in a range of 0.01 to 0.1.

13. The reaction regeneration apparatus according to claim 9, wherein a length of a part of the outlet zone of the fluidized bed reactor that is above the inlet for accelerating gas divided by an overall length of the outlet zone of the fluidized bed reactor is in a range of 0.1 to 0.8.

14. The reaction regeneration apparatus according to claim 8, wherein a guide plate with through holes is disposed between the inlet zone and the reaction zone of the fluidized bed reactor.

15. The reaction regeneration apparatus according to claim 8, wherein the inlet zone of the fluidized bed reactor is disposed lower than the lower region of the damper, and the lower region of the damper is communicated with the inlet zone of the fluidized bed reactor through a first pipe.

16. The reaction regeneration apparatus according to claim 15, wherein the first pipe, the second pipe, and the third pipe each are provided with a valve for controlling material flow.

17. A reaction regeneration apparatus, comprising a separation device, a fluidized bed reactor and a catalyst regeneration device,
wherein the separation device comprises:
a preliminary gas-solid separator communicated with an outlet of the fluidized bed reactor,
a vertically arranged damper, a solid outlet of the preliminary gas-solid separator being communicated with a lower region of the damper, and a gas outlet of the preliminary gas-solid separator being communicated with an upper region of the damper, and
a fine gas-solid separator, an inlet of the fine gas-solid separator being communicated with the upper region of the damper, and a solid outlet of the fine gas-solid swarator being communicated with the lower region of the damper,
wherein the separation device is configured so that product having catalysts entrained therein from the fluidized bed reactor is fed into the preliminary gas-solid separator most solid catalysts being separated and fed into the lower region of the damper: the product entraining the rest catalysts is fed into the upper region of the damper, and into the fine gas-solid separator, the rest catalysts being separated and fed into the lower region of the damper; and final product is obtained from a gas outlet of the fine gas-solid separator;
wherein
the fluidized bed reactor comprises an inlet zone at a lower position, an outlet zone at an upper position, and a reaction zone between the inlet zone and the outlet zone, the outlet zone being communicated with the preliminary gas-solid separator of the separation device, and
the catalyst regeneration device comprises a feed zone at a lower position and a discharge zone at an upper position, the feed zone being arranged lower than the lower region of the damper, and the discharge zone being arranged higher than the inlet zone of the fluidized bed reactor;
wherein, the lower region of the damper is communicated with the feed zone of the catalyst regeneration device through a second pipe, and the discharge zone of the catalyst regeneration device is communicated with the inlet zone of the fluidized bed reactor through a third pipe; and
wherein the third pipe is provided with a flow blocking member at a top of an inner wall thereof.

18. The reaction regeneration apparatus according to clain 17, wherein the flow blocking member is a baffle tilting towards the fluidized bed reactor.

19. The reaction regeneration apparatus according to claim 18, wherein to ratio of an area of the baffle to an area of a cross section of the third pipe is in a range of 0.1 to 1.

20. The regeneration apparatus according to claim 18, wherein the baffle is sector shaped or rectangular.

21. The reaction regeneration apparatus according to claim 18, wherein a ratio of a distance between the baffle and the fluidized bed reactor to a length of the third pipe is in a range of 0.01 to 0.5.

22. The reaction regeneration apparatus according to claim 18, wherein an angle formed between the baffle and an axis of the third pipe is in a range of 10 to 75 degree.

23. The reaction regeneration apparatus according to claim 18, wherein a plurality of baffles is provided, which are arranged in parallel with respect to one another.

24. The reaction regeneration apparatus according to claim 17, wherein the flow blocking member is a stop pawl protruding radially inward.

25. The reaction regeneration apparatus according to claim 24, wherein a plurality of stop pawls is provided, which are arranged in a row along the axis of the third pipe.

26. The reaction regeneration apparatus according to claim 25, wherein a ratio of a length of each stop pawl to a diameter of the third pipe is in a range of 0.1 to 0.5.

27. The reaction regeneration apparatus according to claim 24, wherein a cross section of each of the stop pawls is in a shape of a triangle, a rectangle, or a sector.

28. A process for preparing olefins, using the reaction regeneration apparatus according to claim 8, wherein the inlet zone of the fluidized bed reactor is disposed lower than the lower region of the damper, and the lower region of the damper is communicated with the inlet zone of the fluidized bed reactor through a first pipe,
wherein the process comprises:
reacting raw material containing oxygenates with catalysts in the reaction zone of the fluidized bed reactor,
feeding product obtained and entrained catalysts into the separation device through the outlet zone of the fluidized bed reactor,
separating the product and the entrained catalysts through the separation device, wherein a part of catalysts obtained from the separation is directly fed into the inlet zone of the fluidized bed reactor, and the rest catalysts are regenerated and fed into the inlet zone of the fluidized bed reactor, and
mixing non-regenerated catalysts and regenerated catalysts in the inlet zone of the fluidized bed reactor, and feeding mixed catalysts into the reaction zone of the fluidized bed reactor.

29. The process according to claim 28, wherein a weight ratio of the non-regenerated catalysts to the regenerated catalysts is in a range of 0.3 to 1.5.

30. The process according to claim 28, wherein an operation of the separation device comprises:
preliminarily separating product from the fluidized bed reactor having catalysts entrained therein through the preliminary gas-solid separator,
feeding product obtained from the preliminary separation entraining the rest catalysts into the upper region of the damper,
drawing the product from the damper, and feeding the product into the fine gas-solid separator for fine separation, and
obtaining final product from the gas outlet of the fine gas-solid separator, and gathering catalysts from the preliminary gas-solid separator and the fine gas-solid separator into the lower region of the damper.

31. The process according to claim 30, wherein water vapor is fed into the damper from a lower end thereof, so that product entrained in the catalysts is separated from the catalysts.

32. The process according to claim 28, wherein a pressure in the fluidized bed reactor indicated by gage pressure is in a range of 0-0.4 MPa, an average temperature therein is in a range of 380-550° C, and a mean density in the reaction zone is in a range of 40-200 kg/m$^3$, and
the catalyst used therein is SAPO-34, wherein a catalyst regeneration medium is air and a regeneration temperature is in a range of 600-700° C.

33. The process according to claim 32, wherein an inlet for accelerating gas is disposed in the outlet zone of the fluidized bed reactor, and gas flowing into the outlet zone of the fluidized bed reactor through the inlet for accelerating gas is water vapor or nitrogen, a linear speed of the gas being in a range of 1.0-10.0 m/s.

34. The process according to claim 28, wherein the oxygenates comprises one or more selected from a group consisting of methanol, ethanol, n-propyl alcohol, isopropyl alcohol, C4-C20 alcohol, ethyl methyl ether, dimethyl ether, diethyl ether, diisopropyl ether, methanal, dimethyl carbonate, acetone, and acetic acid, and a weight of the oxygenates accounts for 10 to 100% of the raw material.

35. A process for preparing aromatic hydrocarbons, using the reaction regeneration apparatus according to claim 8,
wherein the process comprises:
reacting raw material containing oxygenates with catalysts in the reaction zone of the fluidized bed reactor,
feeding product obtained and catalysts entrained therein into the separation device through the outlet zone of the fluidized bed reactor, and
separating the product from the catalysts entrained therein in the separation device, wherein the catalysts obtained from the separation is regenerated, and fed into the inlet zone of the fluidized bed reactor, and into the reaction zone of the fluidized bed reactor.

36. The process according to claim 35, wherein an operation of the separation device comprises:
preliminarily separating product from the fluidized bed reactor having catalysts entrained therein through the preliminary gas-solid separator,
feeding product obtained from the preliminary separation entraining the rest catalysts into the upper region of the damper,
drawing the product from the damper, and feeding the product into the fine gas-solid separator for fine separation, and
obtaining the final product from the gas outlet of the fine gas-solid separator, and gathering catalysts from the preliminary gas-solid separator and the fine gas-solid separator into the lower region of the damper.

37. The process according to claim 36, wherein water vapor is fed into the damper from a lower end thereof, so that product entrained in the catalysts is separated from the catalysts.

38. The process according to claim 35, wherein a pressure in the fluidized bed reactor indicated by gage pressure is in a range of 0-0.6 MPa, an average temperature therein is in a range of 440-550° C., a space velocity in the reaction zone is in a range of 0.3-5 h$^{-1}$, and a mean density in the reaction zone is in a range of 200-450 kg/m$^3$, and
the catalyst used therein is ZSM-5, wherein a catalyst regeneration medium is air and a regeneration temperature is in a range of 550-650° C.

39. The process according to claim 38, wherein an inlet for accelerating gas is disposed in the outlet zone of the fluidized bed reactor, and gas flowing into the outlet zone of the fluidized bed reactor through the inlet for accelerating gas is water vapor or nitrogen, a linear speed of the gas being in a range of 1.0-10.0 m/s.

40. The process according to claim 35, wherein the oxygenates comprises one or more selected from a group consisting of methanol, ethanol, n-propyl alcohol, isopropyl alcohol, C4-C20 alcohol, ethyl methyl ether, dimethyl ether, diethyl ether, diisopropyl ether, methanol, din/ethyl carbonate, acetone, and acetic acid, and a weight of the oxygenates accounts for 10 to 100% of the raw material.

* * * * *